(12) United States Patent
Harston et al.

(10) Patent No.: US 6,515,189 B1
(45) Date of Patent: Feb. 4, 2003

(54) REACTIONS OF AROMATIC COMPOUNDS

(75) Inventors: Paul Harston, Salwick (GB); John Burns, Jesmond (GB); Colin Ramshaw, Ponteland (GB)

(73) Assignee: British Nuclear Fuels PLC, Cheshire (GB)

(*) Notice: Subject to any disclaimer, the term of this patent is extended or adjusted under 35 U.S.C. 154(b) by 0 days.

(21) Appl. No.: 09/554,692

(22) PCT Filed: Nov. 5, 1998

(86) PCT No.: PCT/GB98/03288

§ 371 (c)(1),
(2), (4) Date: Feb. 5, 2001

(87) PCT Pub. No.: WO99/22858

PCT Pub. Date: May 14, 1999

(30) Foreign Application Priority Data

Nov. 5, 1997 (GB) .............................................. 9723262

(51) Int. Cl.⁷ ...................... B01J 19/00; C07C 201/08; C07C 205/06
(52) U.S. Cl. ...................... 568/939; 568/940; 422/130; 422/211
(58) Field of Search ................................ 568/927, 932, 568/934, 939, 940; 422/130, 211

(56) References Cited

U.S. PATENT DOCUMENTS 3,976,704 A * 8/1976 Vaughan et al.
4,308,215 A * 12/1981 Vaughan et al.

FOREIGN PATENT DOCUMENTS

| WO | WO 96/12540 | 5/1996 | ............ B01D/11/04 |
|----|----|----|----|
| WO | WO 96/12541 | * 5/1996 | |
| WO | WO 97/00442 | 3/1997 | ............ G01N/30/00 |
| WO | WO 97/14497 | 4/1997 | ............ B01J/19/00 |

OTHER PUBLICATIONS

Liu et al.; "Analytical Chemistry in a Drop. Solvent Extraction in a Microdrop" *Analytical Chemistry* 68:11 1817–1821 (1996).

Mészáros et al.; "Kontinuierlich arbeitende Fadenreaktoren für mikropräparative Zwecke" *Fette, Seifen, Anstrichmittel* 70:12 940–941 (1968). & Translation.

International Search Report for PCT/GB98/03288; mailed on Mar. 22, 1999.

* cited by examiner

*Primary Examiner*—Brian Davis
(74) *Attorney, Agent, or Firm*—Myers Bigel Sibley & Sajovec

(57) ABSTRACT

A method of reacting an aromatic compound with an immiscible reacting agent involves the passage of the reactant along a flow path having a width of from 10 to 1000 $\mu$m in such a way that essentially laminar flow of the reactant takes place. Reaction takes place across the interface between the phases and without substantial mixing of the unreacted aromatic compound and the reacting agents. A preferred reaction is the nitration reaction which involves reaction of a first phase comprising an organic aromatic compound on a second phase comprising a nitrating agent to produce two new phases of different chemical composition to the starting phases. The aqueous and organic phases produced are ideally separated such that minimum contamination occurs. Other examples of this type of reaction include the sulphonation of an aromatic compound using sulphuric acid as the sulphonating agent. The aromatic compound is slowly consumed in the reaction yielding a single aqueous phase.

15 Claims, 3 Drawing Sheets

REACTIONS OF AROMATIC COMPOUNDS

The present invention relates generally to reactions of aromatic compounds. In particular, it relates to methods of carrying out electrophillic substitution reactions on aromatic compounds using microreactors.

Aromatic compounds undergo a number of electrophillic substitution reactions, such as nitration and sulphonation, using a variety of reagents. As an example, aromatic compounds can be nitrated through the use of nitric acid and a catalyst such as sulphuric acid, which are commonly brought into contact with the organic compound to be nitrated in a reactor vessel. The product, a nitroaromatic, then has to be separated from the resulting mixture using some suitable means such as solvent extraction or distillation and the aqueous phase recycled. Such separation procedures add considerable cost and complexity to the process. In addition, undesired by-products may be produced in the reaction, e.g. dinitrobenzene in the formation of nitrobenzene. These by-products may result in further purification of the product.

Numerous micropreparative and microanalytical methods, and corresponding equipment, are available to the chemist. For example, D1: L. MÉSZÁROS & 1. MÉSZÁROS: 'Kontinuerlich arbeitende Fadenreaktoren für mikropräparative Zwecke' FETTE, SEIFEN, ANSTRICHMITTEL., vol. 70, no. 12, 1968, pages 940–941, XP002095576 discloses a thread reactor and its use in the preparation of dinitrobenzene and the sulfonation of decylbenzene. The reactants are fed down two glass threads which are brought together to a single thread where the reactants mix and form an emulsion without any mechanical intervention.

According to the present invention there is provided a method of reacting an aromatic compound with a reacting agent, the method comprising providing a first flow path for the aromatic compound and a second flow path for a reacting agent, the reacting agent being immiscible with the aromatic compound and the flow paths communicating with each other in a region in which the aromatic compound and the reacting agent can contact one another, flowing the aromatic compound and the reacting agent through the first and second flow paths respectively such that, at least in the said region, the flow of the aromatic compound and the reacting agent is essentially laminar, and a stable open interface is formed therebetween, at least the first flow path in the interface region having a width perpendicular to the interface in the range 10–1,000 micrometres, allowing at least a portion of the aromatic compound to react with the reacting agent and flowing the reacted aromatic compound and the reacting agent away from said region, the reaction being carried out without substantial mixing of the unreacted aromatic compound and the reacting agent.

It has been found that the use of a so-called 'microreactor', that is a reactor having a flow path dimension perpendicular to the interface of the two liquid phases of less than 1,000 micrometres, according to the present method, for the nitration of aromatic compounds provides unexpected improvements in process control including significant improvements in both reaction product yield and purity.

The present method also has advantages over conventional methods, in producing an organic product stream which requires no separation from the aqueous reactants and products.

The flow rates of the reactants can also be balanced such that a stoichiometric reaction occurs, thereby resulting in a more efficient and cost-effective process which leaves little or no unreacted reagents which would otherwise reduce the yield of the main product. This also reduces the need for extensive purification procedures for the product.

The flow path carrying the aromatic compound may have a width (defined as perpendicular to the liquid-liquid interface) in the range 10–1,000 micrometres. Preferably, the width lies in the range 30–300 micrometres. Most preferably, the width lies in the range 50–150 micrometres.

The length of the interface region (measured in the direction of the flow) may typically lie in the range 10 mm to 1 metre. For example, a reactor length of 10 centimetres has been used to produce high yields. The optimum reactor length for a particular reaction will be dependant on the flow rates and reaction kinetics in each case.

Typically, the microreactor used in the present method is the same general type of apparatus as disclosed in patent applications WO 96/12541 and WO 96/12540 and the teaching of those documents is incorporated herein by reference.

Patent applications WO 96/12541 and WO 96/12540 disclose the advantages of using microengineered fluid flow paths primarily in solvent extraction processes. Surprisingly, we have found that using the apparatus described in WO 96/12541 and WO 96/12540 to carry out aromatic nitration reactions provides unexpectedly large improvements in both product yield and purity.

The improvements in reaction control provided by the present method are thought to arise from a number of features.

The reacting medium has a high surface area to volume ratio which is thought to allow very efficient heat dissipation to the walls of the reactor. In the case of exothermic reactions, heat generated by the reaction will be carried away from the reacting medium thus reducing the tendency of side products to form. Conversely, the high surface area to volume ratio may also allow efficient transfer of heat into the reacting medium from external sources as required. Thus the microreactor provides an efficient means for heat sinking from or heat sourcing to the fluid reacting region. The high surface area to volume ratio also provides for a high interfacial area for chemical transfer compared with the volume of fluid to be reacted.

The small width of the flow path means that reacting species diffuse over much shorter distances, particularly over distances associated with the diffusion boundary layer width, before they finally react with other reagents than in conventional reactors.

The use of a flow path with a width perpendicular to the liquid interface ranging from 10 to 1,000 micrometres allows very accurate control over very low flow rates. This fine control over flow rate together with precise control over residence time in the reactor provides a highly controllable reacting system which may enable highly reactive intermediate products to be formed in high yield. Such highly reactive intermediates can be difficult to produce under conventional reacting conditions and so may be very valuable. The intermediate may be used in further reactions. The intermediate may be removed from the reactor, or additionally or alternatively, the reaction may be halted before reaching the final product by quenching it with a heat sink or through other methods such as the use of suitable reagents.

The fine fluidic control of the present method also has the advantage of enabling the matching of the input reagents to the correct stoichiometry of the reaction. This can result in a more efficient and cost-effective process which leaves little or no unreacted reagents which would otherwise reduce the yield of the main product. This also reduces the need for extensive purification procedures for the product.

The nitration reaction involves reaction of a first phase comprising an organic aromatic compound on a second phase comprising a nitrating agent to produce two new phases of different chemical composition to the starting phases. The aqueous and organic phases produced are ideally separated such that minimum contamination occurs.

Typically, the nitrating agent is a mixture of nitric acid and sulphuric acid. The reaction is preferably carried out at elevated temperatures, for example, in the nitration of benzene, at 60°–140° C., preferably at 90°–120° C.

The mass concentration of sulphuric acid in the sulphuric acid/nitric acid mixture is typically from 60%–85%, preferably 65%–80% more preferably from 70%–75%. The mass concentration of nitric acid is preferably from 3%–5%.

The organic volume is preferably from 5%–20% of the total and more preferably of the order of 10%.

As indicated above, a preferred reactor length for this nitration reaction is in the range 50 $\mu$m to 150 $\mu$m, such a length taking into account reaction performance on the one hand and pressure drop and blockage factors on the other hand.

Preferred conditions for nitration of aromatic compounds include a sulphuric acid range of 70–75%, about 3% nitric acid, about 10% volumetric organic flow and a temperature of about 100° C. In general the nitric acid content should be balanced with the organic content. Below 5% organic may result in instability and above 20% organic may require excessive quantities of nitric acid, thereby possibly causing DNP to increase and the strength of the sulphuric acid to fall to too low a value.

Other examples of this type of reaction include the sulphonation of an aromatic compound using sulphuric acid as the sulphonating agent. The aromatic compound is slowly consumed in the reaction yielding a single aqueous phase. Reactions of the type with which this invention is concerned may be enhanced by virtue of the short diffusion distances over which the reagents must diffuse. Such diffusion distances are characterised by the expression $Dt/1^2$ where D is the diffusion coefficient, t is the time taken for transport of the reagent before it reacts with the other reagents and 1 is the length scale over which diffusion takes place. For substantial transport (50–100%) of the catalysed reagent, $Dt/1_2$ lies in the range 0.1–1 (see J. Crank—The Mathematics of Diffusion—Second Edition—Oxford University Press, 1975). Typical values of D for liquids lie between $10^{-10}$–$10^{-9}$ m$^2$/s which, for transport times of around 1 second, require length scales and thus reactor dimensions normal to the reactor surface of between 30–100 microns.

The improved reaction control in the present method allows the production of reagents under highly defined conditions. This control will allow hazardous reagents to be produced and controlled such that they are maintained in a safe manner. The reduced inventory of the reagents, both within the lead-in flow paths or microchannels and within the microreactor itself reduces potential risks associated with handling hazardous or explosive reagents.

When large quantities of fluid are required to be reacted, such as in many practical embodiments, a large number of microreactors may be employed. Since large numbers of microreactors may be manufactured relatively cheaply, this provides an efficient way of reacting large quantities of fluid under highly controlled conditions. In addition, in such a"scale-up", the reaction conditions in the microreactors, and hence product distribution, remain unchanged. This is an advantage in comparison to conventional batch reactors where the distribution of products may change as the reaction is scaled up from laboratory-scale to plant-scale.

Examples of apparatus which can be used in connection with the method of the present invention will now be described with reference to the accompanying drawings, in which:

BRIEF DESCRIPTION OF THE DRAWINGS

Referring to FIG. 1 of the accompanying drawings a reactor which may be used in a method of the present invention is shown conceptually. The reactor includes an input channel 1 along which, in use, may be flowed an aromatic compound such as benzene. Input channel 1 opens into a reactor channel 3 as does a further input channel 5 which is a somewhat larger cross-section than channel 1. Channel 5 may carry the other reactant which may be, for instance, an aqueous mixture of nitric acid and sulphuric acid.

Figure 1:
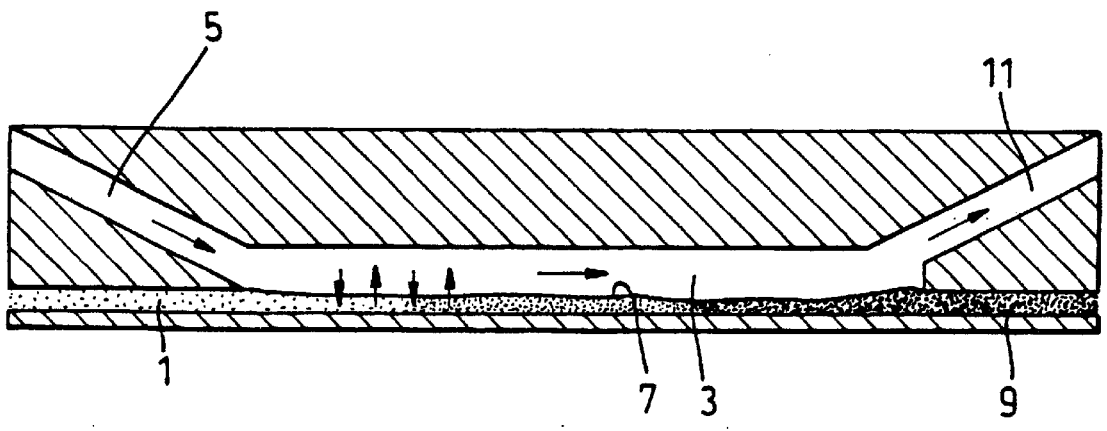
FIG. 1 is a conceptual illustration of a reactor useful in the method of the present invention.

Within reactor channel 3 a laminar flow is established, a stable open interface 7 being formed between the organic and aqueous phases. The liquid flow is indicated by the larger arrows in FIG. 1 and the rapid diffusion across interface 7 is indicated by the smaller arrows.

At the end of reactor channel 3 remote from input channels 1 and 5 are located output channels 9 and 11. Channel 9 receives the organic output whereas the aqueous acid output proceeds along channel 11.

Figure 2:
FIG. 2 is a diagrammatic representation of a reactor useful in the method of the present invention.

Referring to FIG. 2 of the accompanying drawings, there is illustrated more realistically the structure of a reactor suitable for use in a method of the present invention. Organic input is introduced through port 13 and aqueous acid input through port 15. These streams are fed through corresponding channels 17 and 19 respectively into the reactor channel 21 which has a width of 100 $\mu$m. The organic liquid exits from reactor channel 21 into output channel 23 and out of port 24. The aqueous acid exits from reactor channel 21 through output channel 27 and port 29.

Figure 3:
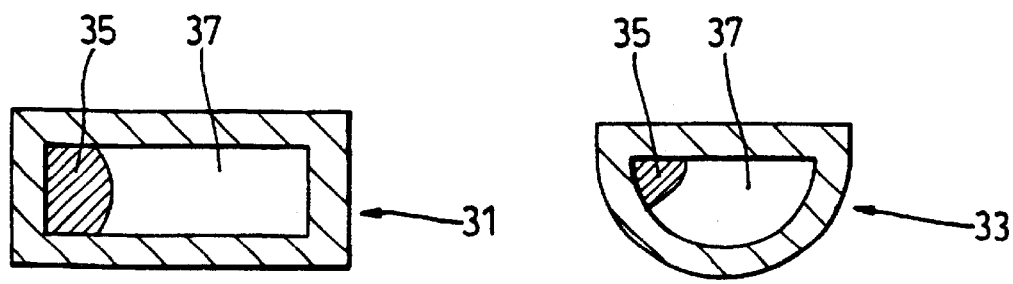
FIG. 3 shows cross-sections through two channels which may form part of reactors useful in the method of the present invention.

FIG. 3 of the accompanying drawings illustrates two typical reactor channel cross-sections, channel 31 having a rectangular cross-section and channel 33 being of semicircular cross-section. Also shown in FIG. 3 are the positions occupied by the organic phase 35 and the acid phase 37 in both reactor channels.

Figure 4:
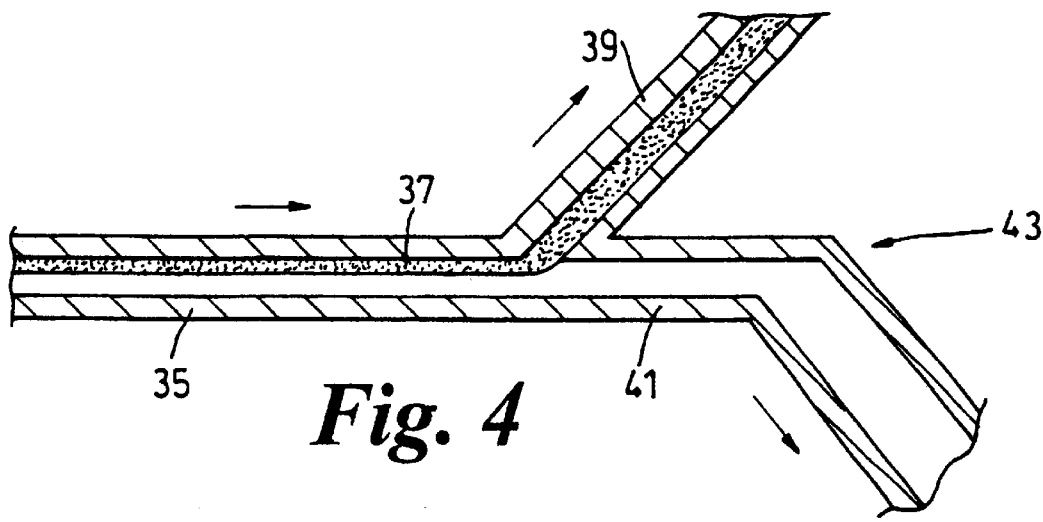
FIG. 4 illustrates a phase splitting at the outlet end of a reactor useful in the method for the present invention.

FIG. 4 of the accompanying drawings illustrates the phase splitting which takes place at the output end of reactor channel 35. As shown, the organic phase 37 flows naturally into output channel 39 which is angled as illustrated from reactor channel 35. The aqueous acid phase enters output channel 41 which extends initially coaxially from reactor channel 35 but then bends as illustrated at 43, the channel becoming of larger width at this position.

Figure 5:
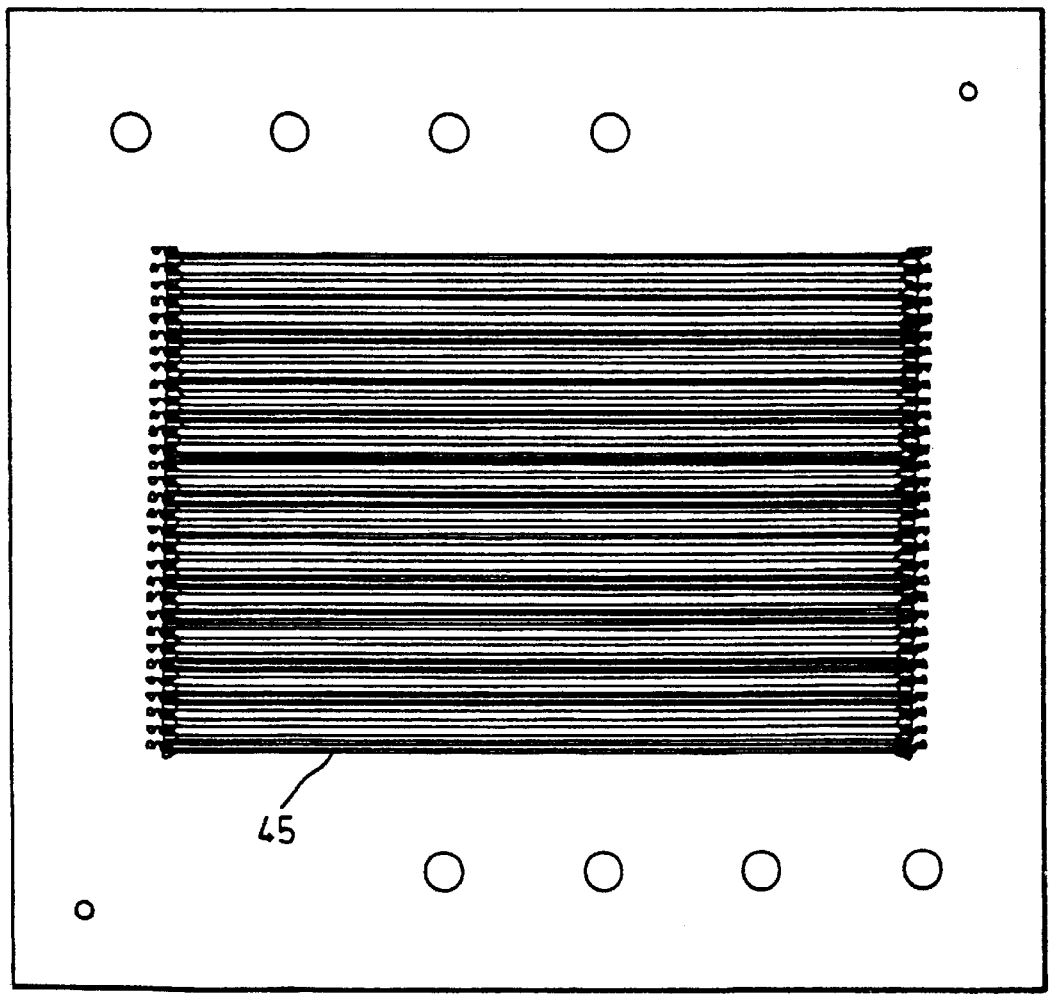
FIG. 5 shows a multichannel reactor sheet which may be used in the method of the present invention.
Figure 6:
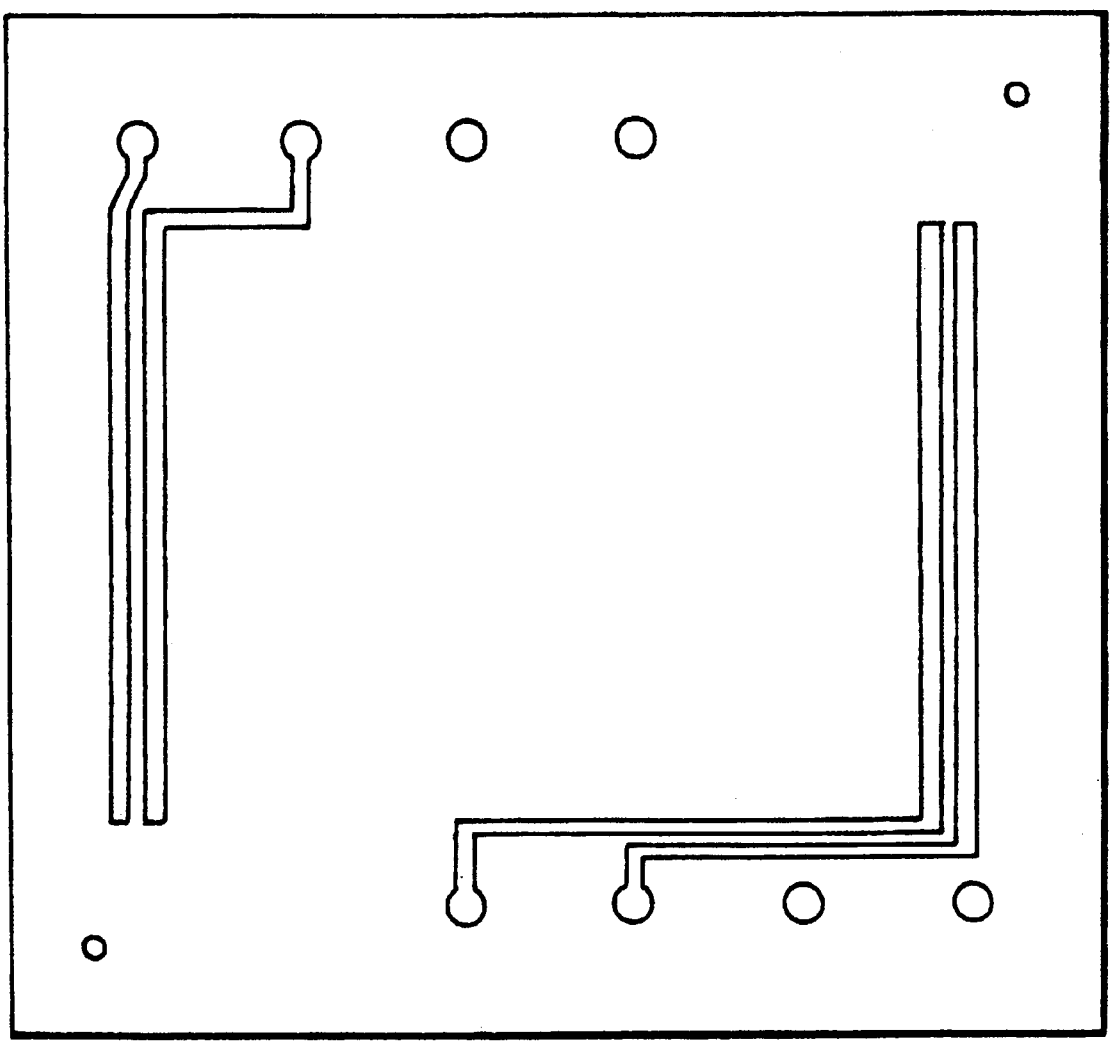
FIG. 6 shows a routing sheet which may form part of the same reactor as that also partly illustrated in FIG. 5.

FIG. 5 illustrates a multichannel reactor sheet, in this case containing 61 reactor channels at 45. The size of the sheet is 130 mm—120 mm. Finally, FIG. 6 shows a routing sheet for delivering liquid into the reactor channels in FIG. 5. The sheet size in this case is also 310 mm×120 mm.

The reactor throughput for the nitration of benzene is typically of the order of 0.1 $\mu$l·s−1 with an acid flow rate of 1.0 $\mu$l·s$^{-1}$. A typical channel density is of the order of 1 channel per mm width. Sheet thickness obtained using etching techniques is of the order of twice the channel width (due to etching from both sides to produce feed holes).

For production scale operation of a method according to the present invention a multichannel reactor might include at least 1,000 channels, perhaps of the order of several thousand channels. A degree of parallel processing may be involved in the manufacture of such reactors. Among the techniques which can be used in order to produce such reactors are the following:

Chemical Etching

Masks are printed onto sheets which contain channel designs. These are then chemically etched, typically using acid, to produce the finished sheet. Some intermediate processing may be required, such as UV exposure, before the etching. Materials that could be used are metals and glass amongst others.

Embossing

A technique suited to polymers where a single tool is produced (possibly by non-parallel techniques such as laser ablation or by x-ray lithography). The tool embosses out many designs on each sheet in a production run.

To assemble the final unit, the sheets may be bonded into a single block using the method of diffusion bonding.

Materials which may be used include PTFE (good chemical resistance and capable of being embossed, stainless steel robust and easy to chemically etch with reasonable chemical resistance; both machinable and weldable) and glass (easy to chemically etch, transparent for visual observation and easily diffusion bonded).

In a typical multichannel reactor unit the sheet thickness may be similar to that of the channel width and is typically in the range 50 $\mu$m to 300 $\mu$m. The number of channels per sheet range from 10 to 1,000 and is typically of the order of 100. There may be from 10 to 1,000 sheets per block typically of the order of 100. Accordingly the number of channels per block may be from 100 to 1,000,000 and is preferably 1,000 to 100,000.

A 15 cm×15 cm×15 cm block containing 1,000 sheets (each 200 $\mu$m thick) of 100 channels with 100 routing sheets will produce 10 ml·s$^{-1}$ of organic output. Continuous running of such apparatus will produce 864 litres·day$^{-1}$ which is equivalent to about 300 tonnes per year.

Specific embodiments of the invention will now be described in detail by way of the following Examples only.

EXAMPLE 1

The formation of nitrobenzene was carried out using a simple reactor with channel widths perpendicular to the liquid-liquid interface of 10–200 microns. The reactor is shown schematically in FIG. 2.

Benzene was flowed through port 13, and an aqueous mixture of nitric acid and sulphuric acid was flowed through port 15. The flow rates of the reactants were balanced such that a stoichiometric reaction occurred. Reaction occurred along the channel and the product, nitro-benzene, was flowed out of port 25. The sulphuric acid and aqueous product was flowed out of port 29. The reactor and flow conditions were such that no aqueous phase contaminated the organic product exiting port 25. No separation of the organic product from the aqueous reactants and products was therefore needed. By-products formed were significantly reduced compared to conventional conditions.

Ideally in this type of reaction only aqueous phase material would leave port 29, but the reactor and conditions could be arranged such that a small proportion of organic leaves port 29.

EXAMPLE 2

Benzene nitration was carried out using a 178 $\mu$m channel, a temperature of 90° C., 78% sulphuric acid and 4.5% nitric acid. The by-product contamination was less than 3,000 ppm dinitrobenzene (hereinafter"DNB") and less than 300 ppm dinitrophenol (hereinafter"DNP").

Benzene nitration carried out with a 178 $\mu$m channel, a temperature of 90° C., 73% sulphuric acid and 4.5% nitric acid resulted in a by-product contamination of less than 500 ppm DNB and less than 100 ppm DNP.

In a benzene nitration reaction carried out with a 178 $\mu$m channel, 90° C., 72% sulphuric acid and 4.5% nitric acid, the time for"complete" conversion was estimated at 50 seconds. In a similar reaction but carried out with 78% sulphuric acid, the time for"complete" conversion was estimated at 25 seconds.

EXAMPLE 3

Toluene nitration was carried out in a glass reactor of 200 $\mu$m×100 $\mu$m at 100° C. with 72% sulphuric acid and 3.0% nitric acid. For a 1 second residence time, 43% conversion was obtained. The isomer output was 57% 2-nitrotoluene, 6% 3-nitrotoluene and 37% 4-nitrotoluene. The time for conversion was estimated at 4 seconds.

What is claimed is:

1. A method of reacting an aromatic compound with a reacting agent, the method comprising providing a first flow path for the aromatic compound and a second flow path for a reacting agent, the reacting agent being immiscible with the aromatic compound and the flow paths communicating with each other in a region in which the aromatic compound and the reacting agent can contact one another, flowing the aromatic compound and the reacting agent through the first and second flow paths respectively such that, at least in said region, the flow of the aromatic compound and the reacting agent is essentially laminar, and a stable open interface is formed therebetween, at least the first flow path in the interface region having a width perpendicular to the interface in the range 10–1,000 micrometres, allowing at least a portion of the aromatic compound to react with the reacting agent and flowing the reacted aromatic compound and the reacting agent away from said region, the reaction being carried out without substantial mixing of the unreacted aromatic compound and the reacting agent.

2. A method as in claim 1 and wherein the width is in the range 30–300 micrometres.

3. A method as in claim 2 and wherein the width is in the range 50–150 micrometres.

4. A method as in claim 1 and wherein the reacting agent is a nitrating agent.

5. A method as in claim 4 and wherein the nitrating agent comprises a mixture of nitric acid and sulphuric acid.

6. A method as in claim 1 and wherein the reacting agent is a sulphonating agent.

7. A method as in claim 6 and wherein the sulphonating agent is sulphuric acid.

8. A method as in claim 1 and wherein the aromatic compound is benzene or toluene.

9. A method as in claim 1 and wherein the reaction is carried out at an elevated temperature.

10. A method as in claim 5 where the mass concentration of sulphuric acid is from 65% to 80%.

11. A method as in claim 10 where the mass concentration of sulphuric acid is from 70% to 75%.

12. A method as in claim 10 wherein the mass concentration of nitric acid is in the range of 3% to 5%.

13. A method as in claim 10 wherein the organic volume is from 5% to 20%.

14. A method as in claim 10 wherein the reaction temperature is from 60° C. to 140° C.

15. A method as in claim 14 wherein the reactor temperature is from 90° to 120° C.

* * * * *

UNITED STATES PATENT AND TRADEMARK OFFICE
CERTIFICATE OF CORRECTION

PATENT NO. : 6,515,189 B1
DATED : February 4, 2003
INVENTOR(S) : Paul Harston, John Burns and Colin Ramshaw It is certified that error appears in the above-identified patent and that said Letters Patent is hereby corrected as shown below:

<u>Title page,</u>
Item [56], OTHER PUBLICATIONS, please enter:
-- Carey et al, Organic Chemistry/Francis A. Carey-$2^{nd}$ ed, McGraw-Hill, Inc. 1992, Page 456. --

Signed and Sealed this

Fifth Day of August, 2003

JAMES E. ROGAN
*Director of the United States Patent and Trademark Office*